US005891842A

United States Patent [19]

Kream

[11] Patent Number: 5,891,842
[45] Date of Patent: *Apr. 6, 1999

[54] METHODOLOGY FOR ELICITING AN ANALGESIC RESPONSE IN A LIVING SUBJECT

[75] Inventor: Richard M. Kream, Wollaston, Mass.

[73] Assignee: Trustees of Tufts College, Medford, Mass.

[ * ] Notice: This patent issued on a continued prosecution application filed under 37 CFR 1.53(d), and is subject to the twenty year patent term provisions of 35 U.S.C. 154(a)(2).

[21] Appl. No.: 631,434

[22] Filed: Apr. 12, 1996

Related U.S. Application Data

[63] Continuation of Ser. No. 44,954, Apr. 9, 1993, abandoned.
[51] Int. Cl.$^6$ .................................................. A61K 38/04
[52] U.S. Cl. ................................................ 514/2; 530/327
[58] Field of Search ................... 514/2, 12, 14, 514/15, 282, 310; 530/327

[56] References Cited

U.S. PATENT DOCUMENTS 4,059,693 11/1977 Stewart ..................................... 514/12

OTHER PUBLICATIONS

Frederickson et al., "Dual Actions of Susstrate P" Science, v. 199, pp. 1359–1361, 24 Mar. 1978.
Hayes & Tyers, Br. J. Pharmac. 66:488P (1979).
Sawynok et al., Neuropharmacology 23:741–747 (1984).
Cridland & Henry, Brain Research 381: 93–99 (1986).
Bossut et al., Brain Research 455:232–239 (1988).
Stachura et al., "Pharmacological Interactions Between Neuropeptides and Morphine . . . ", (1991), Pol. J. Pharmacol. Pharm., v. 43, pp. 459–469.
Chemical Abstracts 117(17):164199g, (1991), Stachura et al.
Chem. Abstr 103–120891H (1985).

*Primary Examiner*—Cecilia J. Tsang
*Assistant Examiner*—Patrick R. Delaney
*Attorney, Agent, or Firm*—Clark & Elbing LLP

[57] ABSTRACT

The present invention provides a method for eliciting an opioidal analgesia in a living subject using two classes of chemical compositions previously thought to have directly contradictory and physiologically antagonistic roles in the spinal analgesic process. The present methodology relies upon a concurrent administration of an opioid in marginal concentrations in combination with marginal doses of substance P or its related entities which function in a synergistic relationship and mechanism of action. The methodology relies upon a powerful potentiation and enhancement of an opioid-mediated response by the enhancing action of substance P to modulate or eliminate pain and other nociceptive responses, as well as inducing anesthesia.

12 Claims, 7 Drawing Sheets

METHODOLOGY FOR ELICITING AN ANALGESIC RESPONSE IN A LIVING SUBJECT

This application is a continuation, of application Ser. No. 044,954, filed Apr. 9, 1993, now abandoned.

RESEARCH SUPPORT

The research investigations of the present invention were supported by Grant Number DA04128 from the National Institute On Drug Abuse and by institutional grants from the Tufts University School of Medicine.

FIELD OF THE INVENTION

The present invention is concerned generally with medical procedures and pharmacologically active compounds able to provide analgesia and/or anesthesia; and is particularly directed to methods for eliciting an opioid analgesic response in a living subject prior to or after the occurrence of a nociceptive event.

BACKGROUND OF THE INVENTION

A nociceptor, by definition, identifies one of the nonadapting free nerve endings typically found in the skin and in the deeper tissues such as the arterial walls, periosteum, and surfaces of joints which responds to one or more types of noxious or damaging stimuli. Such stimuli include extreme temperature and mechanical trauma which are mediated by various chemical agents. Signals from these receptors are perceived primarily within the spinal cord of the Central Nervous System ("CNS") as pain; and the duration of effect is perceived as acute or chronic pain. A nociceptive response is thus mediated by a sensory receptor that responds to noxious and damaging stimuli, which are perceived as painful sensations; it is also a term used to describe a reflex or response to such a noxious stimulus.

Accordingly, nociception or pain is a protective mechanism that occurs when living tissues are threatened or are in the process of being damaged which causes the living individual to react to remove the painful stimulus.

Many research investigations have been reported and much scientific literature exists regarding pain receptors, contributions of the autonomic nervous system to painful stimulation, the transmission of pain signals, the physiological and chemical reactions to pain, and therapeutic methods for treating pain. Representative examples of the extensive literature on the subject are the following: *Textbook Of Pain*, (Wall and Melzack, editors), 2nd Edition 1989; Management Of Pain, (Bonica, J. J., editor), Lea and Febiger, 1953; Clinical Pharmacokinetics Of Analgesic Drugs (Prithri, R. P., editor), Yearbook Medical Publishers, 1986; A Synopsis Of Anesthesia, 10th edition, 1987; Pain, Discomfort and Humanitarian Care, (Bonica, J. J., editor), Elsevier Publishing, 1980; Essentials Of Medicine, W. B. Saunders Company, 1986; Correlative Neuroanatomy and Functional Neurology, (Joseph G. Chusid, editor), Lange Medical Publications, 1985; Pharmacology and Physiology in Anaesthetic Practice, (Robert K. Stoelting, editor), J. B. Lippincott Company, 1991.

From this literature and numerous reported research investigations, a conceptual model of pain transmission has been developed and generally accepted which includes ascending excitatory afferent pain pathways, cortical integration, descending inhibitory pain pathways, and an extensive neurochemistry that includes a variety of different neuromodulators and neurotransmitters [Cousins, N. J. and L. E. Mather, *Anesthesiology* 61:276–310 (1984)]. Basically, nociceptive impulses traveling via afferent nerves from pain receptors enter the dorsal horn of the spinal cord. Then, at this site, i.e., the 1st spinal synapse, a release of excitatory neurotransmitters (such as an 11-amino acid peptide known as substance P) occurs which is necessary for rostral transmission of pain impulses [Yaksh, T. L. and D. L. Hammond, *Pain* 13:1–86 (1982)]. Functionally, it has been noted and demonstrated that the release of substance P into the cerebral spinal fluid is inhibited by prior or concurrent administration of intrathecal morphine [Yaksh, et al., *Nature* 286:155–156 (1980)]. In addition, a depletion of substance P renders animals insensitive to noxious thermal stimuli. Although the generally accepted model of pain transmission includes a complex system of multiple pathways and chemical agents, substance P and opioid alkaloids such as morphine are two prototypic examples of chemical compounds and agents which are commonly recognized by research investigators, clinicians, and other practitioners in this art as having directly antagonistic and completely opposite roles and functions in the mediation of spinal nociceptive processes.

Thus, it is useful here to summarily review the generally recognized chemical characteristics, pharmacological attributes, and functional roles and interactions of opioid alkoids of which morphine sulfate is the prototypic example; and in addition, to review its pharmacological relationship and functional interaction with the tachykinin, substance P (or "SP") in the elicitation and the modulation of a nociceptive response in a living subject. A excellent general review is presented by The *Pharmacological Basis of Therapeutics* [Gilman et al, editors, MacMillan Publishing Company, seventh edition, 1985, Chapter 22, pages 491–531], the text of which is expressly incorporated by reference herein.

Opioids and opioid agonists designate a group of pharmacologically active compounds that are, in varying degrees, opium-or morphine-like or are related in their structure and/or properties. Opioids are employed primarily as analgesics; interact with several closely related types of receptors; and share some properties in common with the endogenous or three naturally occurring families of opioid peptides—i.e., the enkephalins, the endorphins, and the dynorphins. Historically, the physiological effects of opium—the parent of all opioids—have been known for many millennia. Opium is derived from the juice of the poppy; and it was first introduced mainly for the control of dysenteries. The analgesic and anesthetic effects of opium were well recognized by the 16th century, as were the toxic and addictive dangers of opium for the user. Opium contains more than 20 distinct alkaloids, the first of which, morphine, was isolated in 1806. Codeine and papaverine were then recovered in 1832 and 1848 respectively. By the middle of the nineteenth century, the use of partially-pure alkaloids rather than crude opium preparations became the prevalent practice.

Morphine and the morphine-related opioids produce their major effects on the central nervous system ("CNS") and the enteric nervous system. The physiological effects are remarkably diverse and include: analgesia, drowsiness, changes in mood, respiratory depression, decreased gastrointestinal motility, nausea, vomiting, and alterations in endocrine and autonomic function. Furthermore, when morphine or other opioid analgesics are administered for the relief of pain and to provide an antinociceptive effect at the spinal level, the physician must recognize that only symptomatic treatment is being provided and the underlying pathology remains. The physician must therefore constantly weigh the benefits of this immediate relief against its costs and risks to the patient. A major associated risk is that repeated daily administrations of morphine or morphine-like opioids will eventually produce significant tolerance to the therapeutic effects of the drug as well as initiating some degree of physical dependence. The degree of tolerance and physical dependence will vary with the particular opioid employed, the frequency of administration, and the quantity of opioid administered. In addition, the development of psychological dependency is always a major factor. Accordingly, any decision to relieve the symptomology of chronic pain via administration of an opioid may be short sighted and can be an actual disservice to the patient. Furthermore, the physician is constantly cautioned to employ measures other than opioid drugs to relieve chronic or acute pain when such alternative methods are effective and available. Such alternative measures typically include the use of local nerve block, antidepressant drugs, electrical stimulation, acupuncture, hypnosis, or behavioral modification [Reuler et al., *Ann. Intern. Med.* 93:588–596 (1980)].

When given therapeutically, morphine and most opioids are typically administered intravenously or parenterally in milligram (mg) doses and provide a duration of action ranging typically between 1–5 hours. Table A below provides a representative listing of opioid analgesics with respect to dosage and duration of action.

TABLE A

A Comparison of Opioid Analgesics

| NONPROPRIETARY NAME | TRADE NAME | DOSE* (mg) | DURATION OF ACTION* (hours) |
|---|---|---|---|
| Morphine | | 10 | 4–5 |
| Heroin (diacetylmorphine) | | 4 (2–8) | 3–4 |
| Hydromorphone (dihydromorphinone) | Dilaudid | 1.5 | 4–5 |
| Oxymorphone (dihydrohydroxymorphinone) | Numorphan | 1.0–1.5 | 4–5 |
| Metropon (methyldihydromorphinone) | | 3.5 | 4–5 |
| Codeine | | 120 (10–20) | (4–6) |
| Hyrocodone (dihydrocodeinone) | Hycodan | (5–10) | (4–8) |
| Drocode (dihydrocodeine) | SYNALGOS-DC | 60 | 4–5 |
| Oxycodone (dihydrohydroxycodeinone) | | 10–15 | 4–5 |
| Pholcodine (β-morpholinylethylmorphine) | | (5–15) | (4–5) |
| Levorphanol | Levo-Dromoran | 2 | 4–5 |
| Methadone | Dolophine | 8–10 | 3–5 |
| Dextromoramide | Palfium | 5–7.5 | 4–5 |
| Dipipanone | | 20–25 | 4–5 |
| Phenadoxone | | 10–20 | 1–3 |

TABLE A-continued

A Comparison of Opioid Analgesics

| NONPROPRIETARY NAME | TRADE NAME | DOSE* (mg) | DURATION OF ACTION* (hours) |
|---|---|---|---|
| Meperidine | DemeroL | 75–100 | 2–4 |
| Alphaaprodine | Nisentil | 40 | 1–2 |

*Dose shown is the amount given subcutaneously that produces approximately the same analgesic effects as 10 mg of morphine administered subcutaneously. The figures in parentheses are the doses and the duration of action for oral, antitussive doses: they are not necessarily equieffective doses. Duration of action shown is for analgesic effects after subcutaneous administration: after intraveneous administration, peak effects are somewhat more pronounced but overall effects are of shorter duration. The doses and durations shown in this table are reproduced from The Pharmacological Basis of Therapeutics, (Gilmon et al., editors), 7th Edition, MacMillan Publishing Co., 1985, p. 505, and are based primarily on Eddy, et al., Bull, WHO 46:639–719 (1969); Reynolds, A.K. and L.O. Randall, Morphine and Allied Drugs, University of Toronto Press, Toronto, 1957; and Lsagna, L., Pharmacol. Rev. 16:47–83 (1964).

An extensive pharmacological literature has documented the analgesic properties of morphine and morphine related opioid agonists when administered directly at the spinal level [Kitahata, L. N. and J. G. Collins, *Anesthesiology* 54:153–163 (1981); Yaksh T. L., *Pain* 11:293–346 (1981); Cousins, M. J. and L. E. Mather, *Anesthesiology* 61:276–310 (1984)]. Opioid-induced analgesia is mediated by neural networks at several areas within the central nervous system and involves several distinct but interrelated neurotransmitter systems. Although opioids do not alter the threshold or responsivity of afferent nerve endings to noxious stimulation or impair the conduction of the nerve impulse along peripheral nerves, they do decrease conduction and transmission of impulses of primary afferent fibers after entering the spinal cord. In general, opioids depress electrical activity at the spinal level. There are 3 major types of opioid receptors ($\mu$, $\kappa$, $\delta$) on the terminal axons of primary afferents within laminae 1 and 2 of the spinal cord and within the spinal nucleus of the trigeminal nerve. Morphine and morphine-related drugs acting at these sites decrease the release of neurotransmitters, such as substance P, that normally mediate the transmission of pain impulses. Thus, at the spinal level, opioid analgesics directly counteract, contradict, and neutralize the pharmacological activity of substance P as well as other neurotransmitters in-vivo. Neutralization can also be expressed as physiological antagonism; neutralization or physiological antagonism is a major mechanism by which pain relief may be obtained.

In addition, to direct analgesic effects, morphine-like drugs also relieve suffering by altering the emotional component of the painful experience. As a consequence, if little or no emotional support is provided externally—i.e., by biofeedback mechanisms, some patients may require considerably more than the average dose of an opioid to experience any relief from pain; similarly, others may require more frequent administration. Therefore, out of an exaggerated concern for eliminating the possibility of inducing addiction, many physicians frequently tend to prescribe initial doses of opioids that are either too low, or too infrequent a time interval to successfully alleviate pain. Consequently, they respond to the patient's continued complaints of pain with an even more exaggerated concern about dependency. This is done despite the high probability that the request for more opioid is only the expected consequence of the inadequate dosage originally prescribed [Sriwatanakul et al., *J.A.M.A.* 250:926–929 (1983)]. In this regard, it has also been documented that children are probably more apt to receive inadequate dosages for pain than are adults based on the same type of reasoning concerning tolerance and dependence [Schechter, N. L., *Curr. Probl. Pediatr.* 15 (1985)]. Finally, it is useful to remember that the typical initial dose of morphine (10 mg/70 kg body weight) relieves post-operative pain satisfactorily in only about two-thirds of patients [See page 511, Gilman et al., *The Pharmacological Basis of Therapeutics*].

In contrast to the pharmacology of opioids, the undecapeptide substance P ("SP") has long been recognized and identified as a neurotransmitter intimately associated with the transfer of painful or nociceptive stimuli from peripheral receptive fields into the central nervous system [Jessell, T., *Handbook Psychopharmacol.* 16:1–105 (1983); Pernow, B., *Pharmacol. Rev.* 35:85–141 (1983); Helke, et al., *FASEB J.* 4:1606–1615 (1990)]. Substance P is the prototypic member of a family of related peptides named tachykinins, all of which were initially characterized by contractile activity on isolated smooth muscle preparations. After its original discovery by Von Euler and Gaddum [*J. Physiol.* 72:74 (1931)], substance P was found to be present in the brain, spinal cord, spinal ganglia, and intestine of all vertebrates including man. While its various biological activities have long been recognized, the actual amino acid sequence structure and solid-phase synthesis of the peptide was accomplished only in 1971 [Chang et al., *Nature New Biol.* 232:86 (1971)].

Since the specific identification and synthesis of substance P was made and the ensuing availability of the peptide for research investigations occurred, it has been accepted that substance P regulates nociceptive information at the first synapse in the spinal cord—on the basis that it is found in small-diameter sensory fibers which mediate nociceptive inputs, and on the basis that it specifically excites nociceptive neurons in this spinal region [Henry, J. L., *Brain Res.* 114:439–451 (1976); Hokfelt et al., *Brain Res.* 100:235–252 (1975); Torebjork, H. E., *Acta Physiol. Scand.* 92:374–390 (1974)]. This consensus view has been substantiated by considerable evidence; high concentration nerve terminals containing substance P are in opposition to specific receptors for substance P in regions of the dorsal horn where nociception is initially integrated [Hokfelt et al., *Proc. Natl. Acad. Sci. U.S.A.* 74:3081–3085 (1977); Cuello et al., *J. Neurochem.*, 29:747–751 (1977); Quirion et al., *Nature* (London) 303:714–71 (1983); Ruda et al. *Prog. Brain Res.* 66:219–268 (1986)]; substance P is released in the spinal cord in-vivo specifically upon activation of nociceptive primary sensory fibers [Theriault et al, *Brain Res.* 170:202–213 (1979); Brodin et al., *Neurosci. Lett.* 76:357–362 (1987); Go, D. L. W. and T. L. Yaksh, *J. Physiol.* (London) 391:141–167 (1987); Duggan et al., *Brain Res.* 451:261–273 (1988); Cridland, R. A. and J. L. Henry, *Brian Res.* 462:15–21 (1988)]; and the release of substance P is blocked by administration of morphine and opioid peptides in-vivo and in-vitro [Go, V. O. W. and Yaksh, T. L., *J. Physiol.* (London) 391:141–167 (1987); Jessell, T. N. and L. L. Iversen, *Nature* (London) 268:549–551 (1977); Yaksh et al., *Nature* (London) 286:155–157 (1980)].

Furthermore, it has been recognized that direct application of large microgram doses of substance P into the lumbar spinal subarachnoid produces hyperalgesia—i.e., an increased sensitivity to pain [Yasphal et al., *Pain* 14:155–167 (1982); Sawynok et al., *Neuropharmacology* 23:741–747 (1984); Cridland, R. A. and J. L. Henry, *Brain Res.* 381:93–99 (1986)]; and that intrathecal administration of morphine blocks the hyperalgesic effects of intentionally administered substance P [Hylden J. L. K. and G. L. Wilcox, *Eur. J. Pharmacol.*, 86:95–98 (1983); and *J. Pharmacol. Exp. Ther.* 226:398–404 (1983)]. Based on such overwhelming evidence, substance P has long been identified and accepted as a neuromodulator intimately associated with the transfer of painful or nociceptive stimuli [De Koninck, Y. and J. L. Henry, *Proc. Natl. Acad. Sci. USA* 88:11344–11348 (1991); Wiesenfeld-Hallin et al., *Brain Res.* 551:157–162 (1991); Chang et al., *Anesthesiology* 70:672–677 (1989); Nance, P. W. and J. Sawynok, *J. Pharmacol. Exp. Ther.* 240:972–977 (1987); Frenk et al., *Brain Res.* 455:223–231 (1988); Moochhala, S. N. and J. Sawynok, *Br. J. Pharmacol.* 82:381–388 (1984); Marchand et al., *J. Biol. Chem.* 265:264–273 (1990); Shimonaka et al., *J. Neurochem.* 59:81–92 (1992); Kream et al., *Proc. Natl. Acad. Sci. USA* 82:4832–4836 (1985)].

One oddity regarding substance P, however, has been observed and reported. In contrast to the direct spinal effects of substance P, administration of small nanogram doses of this peptide at supraspinal or brainstem sites has been shown to evoke a modest analgesic response [Stewart et al., *Nature* 262:784–785 (1976); Fredrickson et al., *Science* 199:1359–1362 (1978); Malick, J. and J. Goldstein, *Life Sci.* 23:835–844 (1978)]. This evoked effect is presumably caused by a substance P-induced excitation of descending modulatory systems; and has been operationally characterized as opioid-like in nature by virtue of its reversibility by the opioid antagonist naloxone [Naranjo et al., *Peptides* 7:419–423 (1986)]. Thus, a few research investigators have proposed that supraspinal or brainstem administration of substance P secondarily causes the release of endogenous opioid peptides both in the brain stem and the spinal cord, thereby producing an opioid-dependant analgesia. This proposed mechanism is supported by experimental data demonstrating an evoked release of endogenous opioid peptides by substance P [Tang et al., *Neuropharmacology* 22:1147–1150 (1983); Iadarola et al., *Eur. J. Pharmacol.* 121:39, 48 (1986)].

Overall therefore, and with particular respect to therapeutic spinal administrations of morphine and morphine-related opioid agonists, it is generally recognized and long been accepted that substance P and the opioid alkaloids are pharmacologically active compounds which have opposite and directly contradictory roles and functions in the mediation of spinal nociceptive processes. One class of compound is generally recognized to contradict and neutralize the pharmacological activity of the other, both in-vivo and in-vitro. Equally important, current good medical practice and therapeutic procedures support and recommend the long established therapeutic regimen of administering morphine or other opioid agonists as one effective means by which to overcome and relieve both acute and chronic pain and to provide analgesia for the patient. The physician, the clinician, and the research investigator working in this field thus have no factual basis for believing or expecting that opioids and substance P may be employed together in combination to any advantage; and, in particular, may be employed together in a manner where substance P markedly potentiates and enhances the antinociceptive effects of morphine when concurrently administered at the spinal level.

SUMMARY OF THE INVENTION

The present invention provides a method for eliciting an opioid analgesia within a living subject, said method comprising the steps of:

administering at least one pharmacologically active opioid selected from the group consisting of morphine, morphine-related opioid agonists, phenylpiperidine-derived opioid agonists, and endogenous opioid peptides to the living subject at a concentration ranging from about 10 pmol/kg–10,000 pmol/kg of body weight or 10 pmol–1000 pmol total opioid;

concurrently administering at least one enhancing agent selected from the group consisting of substance P and its pharmacologically active precursors, analogues, fragments, and derivatives to the living subject at a concentration ranging from about 0.1 pmol/kg–100 pmol/kg of body weight or 1.0 pmol–1000 pmol total; and waiting a determined time period for said administered enhancing agent to interact with and enhance the pharmacological activity of said administered opioid such that an opioid analgesia results within the living subject.

BRIEF DESCRIPTION OF THE FIGURES

The description of the present invention may be more easily appreciated and understood when taken in conjunction with the accompanying drawing, in which.

DETAILED DESCRIPTION OF THE INVENTION

Figure 1:
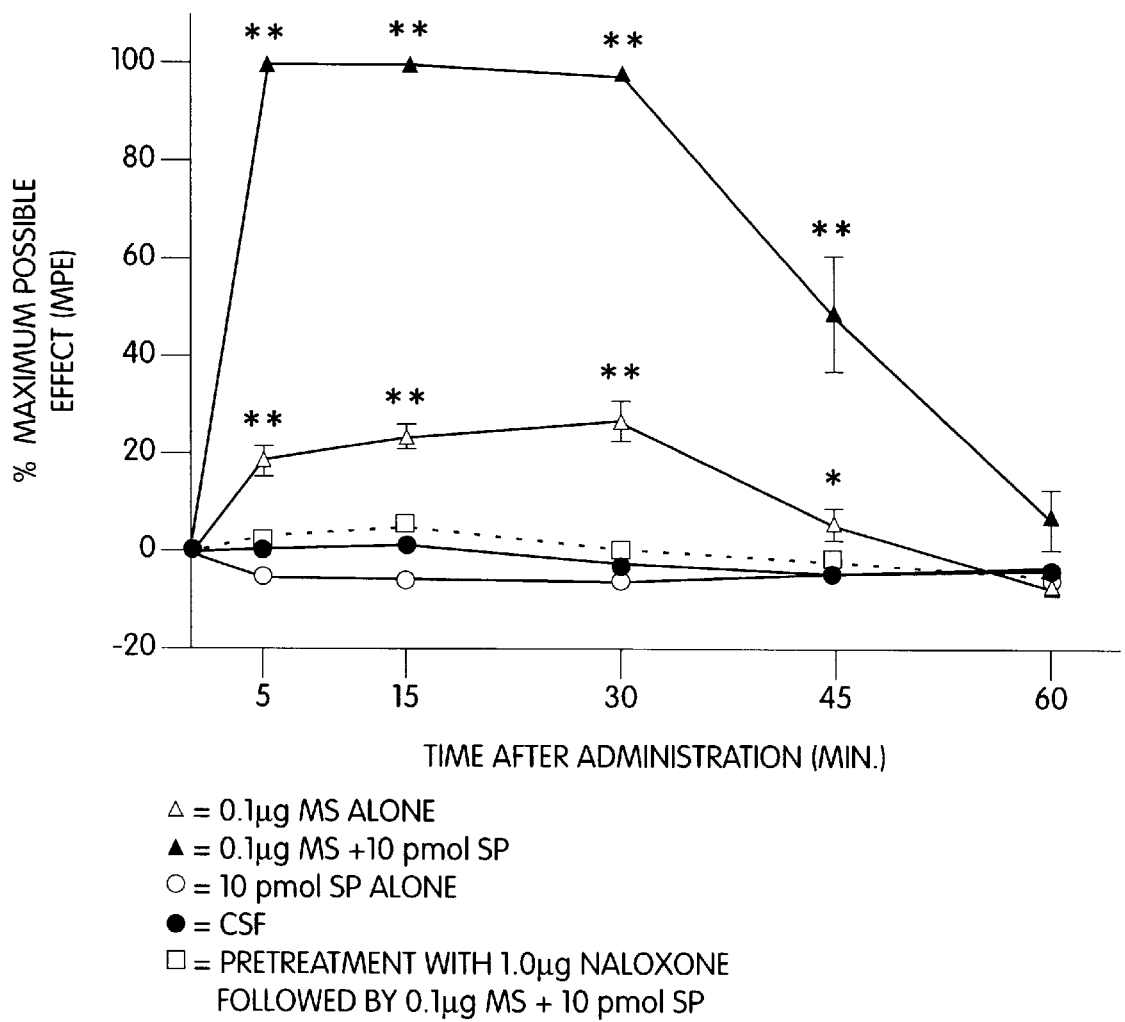
FIG. 1 is a graph illustrating the time-dependant analgesic response of live rats after intrathecal administration of 0.1 ug of morphine sulfate alone or in combination with 10 pmol of substance P.

The present invention is a therapeutic procedure or treatment regimen for inducing or eliciting an opioid-dependent analgesic response within a living subject. The treatment methodology employs and concurrently administers two recognized self-contradicting and physiologically antagonistic compounds at individual concentrations which have been empirically shown to have either marginal or completely ineffectual pharmacological properties in-vivo. Nevertheless, despite the apparent contradiction and direct physiological antagonism between these compounds in their traditional formats and conventionally used concentrations, the present treatment process and methodology combines these compositions at subpharmacological doses and allows the enhancing agent to interact with the administered opioid such that, after an initial lag period of time, an effective and efficacious opioid-induced analgesia results within the living subject.

The present invention thus provides multiple unique benefits and unusual advantages to the physician, the clinician, and the intended patient. These include the following:

1. The present methodology employs pharmacologically active opioids at concentrations ranging from about 10 pmol/kg to about 10,000 pmol/kg of body weight if the opioid is administered parenterally. Alternatively, 10 pmol–1,000 pmol total opioid is acceptable if the opioid is administered spinally into the subarachnoid space or by the epidural route. This range of use opioid concentrations, if administered in-vivo alone, is clearly ineffectual or provides marginal activity at best. It will be recognized and appreciated that conventional, good medical practices employ opioids at use concentrations in the milligram ($10^{-3}$ gram) or micromolar ($10^{-6}$ molar) range; and that such milligram or micromolar administration of opioids provides an analgesic effect only for a limit of 5 hours duration. In comparison, the use of picomole ($10^{-12}$ moles) represent such a minute quantity of pharmacologically active material that little or no physiological effect is observed. As a consequence, therefore, the conventional risks of toxicity and addiction have been so reduced as to render their probability to be effectively nil.

2. The present methodology intends that any type of morphine-related natural opioid, synthetic morphine congener, phenylpiperidine derivative, or endogenous opioid peptide may be employed in the therapeutic regimen. The preferred opioid is morphine sulfate as pharmaceutically prepared and commercially sold today. However, a wide range and variety of different of opioid analogs and agonists of morphine sulfate may be substituted and employed as the need or desire of the physician or clinician dictate. In particular instances, the naturally occurring opioid peptides comprising enkephalins, endorphins, and dynorphins may be employed to advantage as well. All of these cumulatively and collectively form a single class and membership whose individuals share many closely related attributes, chemical characteristics, and pharmacological properties.

3. The present invention employs at least one enhancing agent selected from the group consisting of substance P and its pharmacologically active precursors, analogs, fragments, and derivatives. Substance P is a well documented and described chemical entity which has been investigated, characterized and observed for many years. Similarly, its precursors, analogs, fragments and derivatives have been the subject of numerous research investigations reported in the scientific literature; have been prepared and purified using a variety of conventionally known techniques and procedures; and are commonly available to many different persons from commercial sources. Collectively and cumulatively, these chemical entities form a single class whose membership share many common characteristics, chemical attributes, and pharmacological properties. Thus, the physician or clinician may choose among the entire membership of such enhancing agents and make a personal selection as his patient's needs or personal wishes dictate.

4. The class of enhancing agents consisting of substance P and its pharmacologically related entities are employed at a concentration ranging from about 0.1 pmol/kg to about 100 pmol/kg of body weight if the enhancing agent is administered parenterally. Alternatively, 1.0 pmol–1,000 pmol total of enhancing agent is employed if administered spinally into the subarachnoid space or by epidural route. It will be recognized and appreciated that this picomolar range concentration lies far outside the conventional uses which have been traditionally employed in-vitro and in animal studies. For example, even in those reported research investigations describing the action of substance P in the evoked release of endogenous opioid peptides, nanomolar ($10^{-9}$ molar) concentrations were always utilized. Thus, the present invention limits the physiological consequences in-vivo of using substance P and its related entities by limiting the range of concentrations to picomole concentration usage.

5. The present invention provides both evidence as well as the means for pharmacologically antagonizing the opioid analgesia elicited within a living subject using the present invention. As will be empirically demonstrated hereinafter, this analgesia is naloxone reversible. Thus, naloxone and the other conventionally known opioid antagonists may be employed as neutralizing or counteracting reagents to diminish or eliminate entirely the opioidal analgesia if desired and on-demand.

6. The present invention relies upon a synergistic enhancement and potentiation of opioids such as morphine sulfate using substance P and its related family members. The degree of enhancement and the increase in potency has been empirically demonstrated to be easily 6 fold. Even when combined in less than optimal concentrations and ratios, and 2 fold increase in potency was observed. The present invention is thus able to provide effective and efficacious analgesia using combinations of compounds previously believed to be self-contradictory and using individual concentrations of these compounds which are considered to be marginal or relatively ineffective. The living subject thus benefits doubly not only by not reducing the usual risks and safety hazards associated with the use of opioids but also by relying on the interaction of these compounds in minute quantities to elicit a durable analgesic effect in a manner which only minimally disturbs and interrupts the normal metabolic processes of the body.

In order to provide a more complete and detailed understanding of the present invention, the disclosure will be presented in the following sequential order; a detailed description of the opioids suitable for use; a detailed description of substance P and its related entities; the routes and manner of administration to the living subject; and experiments with empirical data evidencing and supporting the in-vivo efficacy of the present invention. Each of these sections will be presented seriatim.

I. Opioids

The opioids intended for use within the present methodology are those pharmacologically active compounds selected from the group consisting of morphine, morphine-related opioid agonists (naturally occurring and synthetic), phenylpiperidine derivatives, and endogenous opioid peptides. Cumulatively and collectively these form a single class which share common attributes and pharmacological properties which converge through action at biochemically well-defined receptors.

As regards morphine and the naturally occurring or synthetic, morphine-related opioid agonists, one representative listing has been presented previously herein by Table A. Supplementary and complimentary to this listing is the information provided by Tables 1–3 respectively which present a greater range and variety of chemical entities as well as some detailed chemical structural information for these opioids.

TABLE 1

Opioids And Some Representative Opioid Analogs

| Class/Name | References |
|---|---|
| (1) Morphine sulfate "μ" Opioid Alkaloid Agonists: | |
| (2) Dihydromorphine | Reynolds, A.K., and |
| (3) Hydrocodone | L.O. Randall, Morph- |
| (4) Oxymorphone | ine and Allied Drugs, |
| (5) Fentanyl citrate | Toronto, 1957; Martin, |
| (6) Sulfentanil | W.R., Pharmacol. |
| (7) Meperidine | Rev; 19:463–521 |
| | (1976); and Martin, |
| | W.R., Pharmacol. |
| "κ" Opioid Alkaloid Agonists: | Rev. 35:283–323 (1983). |
| (8) Butorphanol | Martin, W.R., Pharma- |
| (9) Bremazocine | col. Rev. 35:283–323 |
| (10) U-50,488 | (1983); Corbett, A.D. |
| (11) U-69,593 | et al., in Handbook |
| | of Experimental |
| | Pharmacology: |
| Naturally-Occuring Opioid Peptides That Bind To And Activate "μ" and "δ" Opioid Receptors | Opioids, Heidelberg, 1991; and Snyder, S.H., Science 224: 22–31 (1984). |
| (12) Met-enkephalin; [Tyr—Gly—Gly—Phe—Met] | Herkenham, M., and C.B. Pert, J. Neur- |
| (13) Leu-enkephalin; [Tyr—Gly—Gly—Phe—Leu] | osci. 2:1129–1149 (1982); Lewis, R.V., |
| (14) Met-enkephalin-Arg—Phe; [Tyr—Gly—Gly—Phe—Mey—Arg—Phe] | and A.S. Stern, Ann. Rev. Pharmacol. Tox- |
| (15) Met-enkephalin-Arg—Gly—Leu; [Tyr—Gly—Gly—Phe—Met—Arg—Gly—Leu] | icol. 23:353–372 (1983); Beaumont, A. |
| (16) Beta-Endorphin | et al., J. Neurochem. |
| Naturally-Occurring Opioid Peptides That Bind To And Activate "κ" Opioid Receptors: | 44:934–940 (1985); and Hollt, V., Ann. Rev. Pharmacol. Toxi- col. 26:59–77 (1986). |
| (17) Dynorphin A (1–17) | Weber, E. et al., |
| (18) Dynorphin A (1–8) | Nature 299:77–79 |
| (19) Dynorphin B | (1982); Hollt, V. Ann. |
| (20) Alpha-Neoendorphin | Rev. Pharmacol. |
| | Toxicol. 26:59–77 |
| | (1986); and Herman, |
| | B.H., and A. Gold- |
| | stein, J. Pharmacol. |
| | Expt. Ther. 232:27– |
| | 32 (1985). |

TABLE 2

Structures of Morphine And Opiod Agonists
Chemically Related to Morphine

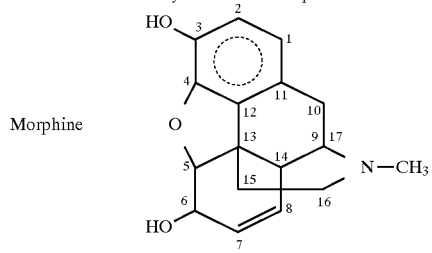

Morphine

CHEMICAL RADICALS AND POSITIONS

| Nonproprietary Name | 3* | 6* | 17* | Other Changes† |
|---|---|---|---|---|
| Morphine | —OH | —OH | —CH$_3$ | — |
| Heroin | —OCOCH$_3$ | —OCOCH$_3$ | —CH$_3$ | — |
| Hydromorphone | —OH | =O | —CH$_3$ | (1) |
| Oxymorphone | —OH | =O | —CH$_3$ | (1), (2) |
| Levorphanol | —OH | —H | —CH$_3$ | (1), (3) |
| Codeine | —OCH$_3$ | —OH | —CH$_3$ | — |
| Hydrocodone | —OCH$_3$ | =O | —CH$_3$ | (1) |
| Oxycodone | —OCH$_3$ | =O | —CH$_3$ | (1), (2) |

*The numbers 3, 6 and 17 refer to positions in the morphine molecule, as shown above
†Other changes in the morphine molecule are as follows:
(1) Single instead of double bond between C7 and C8.
(2) OH added to C14.
(3) No oxygen between C4 and C5.

TABLE 3

Chemical Structures of Opioids Analgesics
Based On Phenylpiperidine

Phenylpiperidine structure with R$_1$, R$_2$*, R$_3$ substituents on piperidine ring attached to phenyl group.

| COMPOUND | R$_1$ | R$_3$ |
|---|---|---|
| Meperidine | —CH$_3$ | —COCH$_2$CH$_3$ (‖ O) |
| Alphaprodine | —CH$_3$ | —OCCH$_2$CH$_3$ (‖ O) |
| Diphenoxylate | —CH$_2$CH$_2$—C(phenyl)—CN | —COCH$_3$ (‖ O) |

TABLE 3-continued

Chemical Structures of Opioids Analgesics
Based On Phenylpiperidine

Phenylpiperidine structure with R$_1$, R$_2$*, R$_3$ substituents.

| COMPOUND | R$_1$ | R$_3$ |
|---|---|---|
| Fentanyl | —CH$_2$CH$_2$—(phenyl) | —N—C(=O)—CH$_2$CH$_3$ with phenyl |

*R$_2$ = H, except in alphaprodine, where R2 = CH$_3$

Studies of the binding of opioid drugs and peptides to specific sites in brain and other organs have demonstrated the existence of perhaps as many as eight different types of opioid receptors. In the central nervous system, there is firm evidence that three (3) major categories of opioid receptors-designated μ, κ, and δ mediate significant biological effects. Although there is considerable variation and the binding characteristics and anatomical distribution of these receptor types analgesia has been associated with all three receptors. The observations in man are consistent with many aspects of this classification of opioid receptors from animal studies. Thus, the actions of opioid drugs that are conventionally known and currently available have usually been interpreted with respect to the participation of these three types of receptors—μ, κ, and δ; and that a given opioid agonist, whether natural or synthetic, may react with any or all of these on an individual basis.

In addition, it will be noted and appreciated that three distinct families of endogenous opioid peptides have been identified and characterized; the enkephalins, the endorphins, and the dynorphins. Each family is derived from a genetically distinct precursor polypeptide and has a characteristic anatomical distribution endogenously. Moreover, within each family, a number of different variants arising from enzymatic processing of the specific precursor at the amino-terminus and/or the carboxyl-terminus have been identified and characterized. Accordingly, all of these variants are encompassed within the terminology and the scope of endogenous opioid peptides.

Although the dosages and concentrations suitable and efficacious for use will vary with the individual chemical entity chosen, the range of opioid concentration will vary from about 10 picomoles per kilogram to about 10,000 picomoles per kilogram of body weight in the living subject if the opioid is administered subcutaneously or parenterally; or be in the range of about 10 pmol to about 1,000 pmol total opioid if administered spinally into the subarachnoid space or given by the epidural route. A preferred range, based primarily on the data observed using morphine sulfate lies within the 10–100 pmol/kg range for subcutaneous or parenteral administration.

II. Substance P and Its Pharmacologically Active
    Precursors, Analogs, Fragments and Derivatives The history, isolation, identification, and synthesis of substance P and its representative family members including precursors, fragments, analogs and/or derivatives have been described in detail previously herein and are conventionally known in this art through numerous scientific publications over many years. Accordingly, all of these different compounds are deemed to be conventionally known and have been utilized for a variety of divergent purposes previously; and the physician, clinician, and pharmacist as well as the research investigator has both the knowledge and confidence to synthesize or otherwise obtain any and all of these different compounds or compositions individually as the need or desire arise.

Substance P is an 11 amino acid peptide which has a number of different natural and synthetic precursor forms; has been demonstrated to be converted into a variety of naturally occurring amino-terminal peptide fragments; and can be obtained in analog format compromising D-amino acids or disulfide bridges substitutions, thereby yielding more stable and discriminating formulations. A representative listing of substance P and its related family chemical entities is provided by Table 4 below.

TABLE 4

Substance P, And Representative Precursors, Fragments, And Stabilized Or Substituted Analogs

| Family Member/Name | Formula |
|---|---|
| (1) Substance P | Arg—Pro—Lys—Pro—Gln—Gln—Phe—Phe—Gly—Leu—Met—amide |
| Natural Precursors: | |
| (2) Substance P—Glycine* | Arg—Pro—Lys—Pro—Gln—Gln—Phe—Phe—Gly—Leu—Met—Gly |
| (3) Substance P—Glycine—Lysine* | Arg—Pro—Lys—Pro—Gln—Gln—Phe—Phe—Gly—Leu—Met—Gly—Lys |
| (4) Substance P—Glycine—Lysine—Arginine* | Arg—Pro—Lys—Pro—Gln—Gln—Phe—Phe—Gly—Leu—Met—Gly—Lys—Arg |
| Carboxy-Ester Synthetic Precursors: | |
| (5) Substance P—Glycine Methyl Ester° | Arg—Pro—Lys—Pro—Gln—Gln—Phe—Phe—Gly—Leu—Met—Gly—OMe |
| (6) Substance P—Glycine—Lysine Methyl Ester° | Arg—Pro—Lys—Pro—Gln—Gln—Phe—Phe—Gly—Leu—Met—Gly—Lys—OMe |
| (7) Substance P—Glycine—Lysine Arginine Methyl Ester° | Arg—Pro—Lys—Pro—Gln—Gln—Phe—Phe—Gly—Leu—Met—Gly—Lys—Arg—OMe |
| (8) Substance P—Glycine—Ethyl Ester° | Arg—Pro—Lys—Pro—Gln—Gln—Phe—Phe—Gly—Leu—Met—Gly—OEth |
| (9) Substance P—Glycine—Lysine Ethyl Ester° | Arg—Pro—Lys—Pro—Gln—Gln—Phe—Phe—Gly—Leu—Met—Gly—Lys—OEth |
| (10) Substance P—Glycine—Lysine—Arginine Ethyl Ester° | Arg—Pro—Lys—Pro—Gln—Gln—Phe—Phe—Gly—Leu—Met—Gly—Lys—Arg—OEth |
| Naturally-Occurring Amino-Terminal Peptide Fragments: | |
| (11) Substance P/1–4# | Arg—Pro—Lys—Pro |
| (12) Substance P/1–7# | Arg—Pro—Lys—Pro—Gln—Gln—Phe |
| (13) Substance P/1–9# | Arg—Pro—Lys—Pro—Gln—Gln—Phe—Phe—Gly |
| Analogs Comprising Synthetic D—Amino Acids Or Disulfide (Cys—Cys) Bridges: | |
| (14) [D—Pro2, D—Phe7, D—Trp9]—Substance P$^{\text{æ}}$ | Arg—D—Pro—Lys—Pro—Gln—Gln—D—Phe—Phe—D—Trp—Leu—Met—amide |
| (15) [D—Pro2, D—Phe7, D—Trp9]—(Substance P—(Glycine$^{\text{æ}}$ | Arg—D—Pro—Lys—Pro—Gln—Gln—D—Phe—Phe—D—Trp—Leu—Met—Gly |
| (16) [D—Pro2, D—Trp7, D—Trp9]—Substance P$^{\text{æ}}$ | Arg—D—Pro—Lys—Pro—Gln—Gln—D—Trp—Phe—D—Trp—Leu—Met—amide |

TABLE 4-continued

Substance P, And Representative Precursors,
Fragments, And Stabilized Or Substituted Analogs

| Family Member/Name | Formula |
| --- | --- |
| (17) [D—Pro2, D—Trp-7, D—Trp9]— Substance P— Glycine[e] | Arg—D—Pro—Lys—Pro—Gln—Gln—D—Trp—Phe—D—Trp—Leu—Met—Gly |
| (18) [Cys3, Cys6, Tyr8, Pro10]— Substance P[f] | Arg—Pro—Cys—Pro—Gln—Cys—Phe—Tyr—Gly—Pro—Met—amide (Cys3 and Cys6 bridged) |

*Shimonka et al., J. Neurochem. 59:81–92 (1992).
°Lee et al., Eur. J. Biochem. 114:315–327 (1981); Pernow, B., Pharmacol. Rev. 35:86–138 (1983); and Regoli et al., TIPS 9:290–295 (1988).
Stewart et al., Nature 262:784–785 (1986); and Skilling et al., J Neurosci. 10:1309–1318 (1990).
[e]Lavielle et al., Biochem. Pharmacol. 37:41 (1988); and Quirion, R. and T.V. Dam, Regulatory Peptides 22:18 (1988).

When one or more of these enhancing agents is concurrently administered by the subcutaneous or parenteral route to the living subject, the agent should be presented at a concentration ranging from about 0.1–100 pmol/kg of body weight and preferably is present at a concentration ranging between 10–100 pmol/kg of body weight. Alternatively, if concurrently administered by the spinal or the epidural route, the enhancing agent is desirably administered in the range of 1.0–1,000 pmol total peptide. Moreover, it is highly desireable that the enhancing agent selected (be it substance P or any of its related family member entities) be preferably present in a stoichiometric proportional ratio of 1:30–1:60 with respect to the concentration of opioid employed. This stoichiometric proportional range is preferred because it has been empirically evidenced (as demonstrated by the experiments presented hereinafter) that a potency range increase of at least 6 fold can be obtained under these use circumstances. However, a range of enhancing agent to opioid ratios from about 1:10 to 1:100 is expected to be advantageous. Accordingly, although efficacious results and an opioidal analgesia can be elicited using proportional ratios of enhancing agent and opioid outside these stated ranges, this interval of proportional ratios will provide an efficacious result repeatedly and consistently.

III. Physiologically Compatible Preparations

Pharmaceutical formulations of the chosen opioid (such as morphine) and of the chosen enhancing agent (such as substance P) include any biocompatible or physiologically appropriate carrier which will permit concurrent administration of each pharmacologically active composition and ingredient. The present invention intends that either and/or both of the administrations employ pharmaceutical formulations and preparations which will permit the chosen dosage/concentration to be administered in the desired route, using conventionally known procedures and techniques as well as to vary and be dependent upon the age, health, and weight of the intended living recipient; the kind of concurrent treatment, if any; the selected frequency of treatment; and the depth and duration of the analgesic response desired.

It is expected also that the chosen opioid will be typically prepared as a water soluble preparation. For example, if the preferred embodiment of morphine is chosen, it is highly desireable that the morphine be prepared as morphine sulfate, which is recognized as being highly water soluble. Similarly, it is most desireable that the enhancing agent, be it substance P or any of its related family member entities, also be prepared in a manner which is highly water soluble. Accordingly, in these water-soluble prepared forms, each of these compounds can be prepared in sterile form; as multiple or single dose formats; and be dispersed in a fluid carrier such as sterile physiological saline or 5% dextrose solutions commonly used with injectables. Finally, it is intended and expected that all pharmaceutically acceptable preparations be prepared and formulated with or without such preservatives, surfactants, and other exicipents as are usual and customary in the making of such preparations.

IV. Routes of Administration

The present invention requires only that the chosen opioid and the chosen enhancing agent be concurrently administered. A preferred mode of concurrent administration is that these chemical compositions be coadministered simultaneously to the living subject. Alternatively, the concurrent administration expects and intends that the administration of one of these compositions precede the other with little or no meaningful delay time between the administration of the second requisite compound. As employed herein, therefore, the term "concurrently" denotes and connotes simultaneous, parallel, sequential, and serial administrations without discriminating among them.

Concerning molar concentrations, 1 pmol=$1 \times 10^{-12}$ moles. Moles in scientific terminology represent the molecular weight of a compound expressed in grams. For the purposes of this invention, conventional administration of milligram amounts of opioids are equivalent to micromolar ($10^{-6}$ molar) concentration. A milligram amount or micromolar concentration thus represents approximately a 1000× higher concentrations than the pmol concentrations used by the present invention.

Several routes of administration are available to the physician or clinician in order to practice the present invention. Administration may be parenteral using any conventionally known means for such parenteral introduction including intravenous injection, perfusion, and the like; and can be subcutaneous if needed or desired. Alternatively, the route of administration may be directly at the spinal level into the subarachnoid space or be epidural in mode using conventionally known apparatus techniques for this purpose. Accordingly, spinal or epidural injection by syringe or other infusion of the requisite chemical entities is appropriate and desirable.

In general, a typical regimen of treatment will concurrently administer the opioid and enhancing agent three times daily; and each concurrent administration is expected to provide 6–8 hours of durable analgesia, when given within the ranges of dose concentration and ratio as stated herein. No complications, contradictions, or unusual safety hazards are foreseen if good medical practices and procedures now customarily in use are employed and observed.

V. Experiments and Empirical Data

To evidence both the usefulness and efficacy of the present invention as a therapeutic technique able to elicit an analgesic response in a living subject, a number of in-vivo experiments using living rats as a representative animal model system have been performed. While the details of the experiment and the results empirically obtained are described in detail below, it is valuable to recognize and appreciate the following: (1) that the in-vivo experiments conducted constitute and employ a validated model system and paradigm in which the living rats react to the administered compositions in a manner which is recognized as being directly comparable to the living human condition; and (2) that the empirical data observed and reported below are of such import and statistical significance that these empirical data in and of themselves are persuasive as direct evidence that similar results are both foreseeable and predictable in outcome if and when human clinical trials are actually performed. The experiments described and the empirical data reported below are thus entirely representative of those results and effects expected and foreseeable in the living human circumstance of use; and provide an probative and factual body of evidence as well as the basis for a reasonable degree of confidence and certainty in outcome when living humans require elicitation of an opioid analgesic effect.

Methods

Cannula implantation: All experimental procedures employed in the present study were approved by the Tufts University Animal Research Committee, protocol # 226-90. Adult male Sprague-Dawley rats, weighing 275–300 g, were anesthetized by intramuscular administration of ketamine (100 mg/kg)/xylazine (10 mg/kg) and implanted with chronic indwelling intrathecal catheters according to a modification of the procedure of Yaksh and Rudy [*Physiol. Behav.* 17:1031–1036 (1976)]. Briefly, after opening the dura at the atlanto-occipital junction, a catheter was inserted for a distance of 8.5 cm. thereby positioning the tip near the L1–L2 lumbar spinal level. The catheter consisted of Silastic tubing (O.D.=0.625 mm, I.D.=0.30 mm, # 602-105, Dow Corning, Midland, Mich.) with less than a 10 ul dead volume into which a style (fused silica, # 062442, Scientific Glass Engineering Inc., Austin, Tex.) was inserted to within 0.5 cm of the catheter tip in order to stiffen the Silastic tubing and to facilitate threading of the catheter through the intrathecal space. After placement, the stylet was removed and the catheter was secured by means of dental cement to stainless steel screws implanted in the skull. The catheter was then plugged with a stainless steel insert and threaded through the skin via a separate small opening lateral to the main skin incision leaving a 3 cm external length. Following surgery, animals were individually housed to insure the patency of the catheter in a temperature and light controlled environment, with free access to food and water. Animals exhibiting any sign of neurological or motor deficit were excluded from the study. After completion of drug testing, verification of catheter position was performed in each animal by postmortem examination of the spinal cord.

Transection of the spinal cord: To assess whether the effects of the combined drug regimen were spinally mediated, a separate group of rats was surgically treated to achieve an acute transection of the spinal cord. These animals had been previously implanted with indwelling cannulae and were fully habituated to the testing apparatus (above). Briefly, animals were anesthetized with 1.5% halothane, and a laminectomy was performed at the level of the second thoracic vertebrae. After opening of the dura, the spinal cord was completely transected without affecting the patency of the intrathecal cannula. The would was closed in layers and animals were allowed to recover from the anesthesia for approximately two hours before administration of drugs. Immediately after completion of drug testing, animals with spinal cord transections were sacrificed by lethal injection of nembutal. For each animal, verification of the completeness of transection was achieved by postmortem examination of the spinal cord.

Drugs: Tested compounds were dissolved in artificial cerebrospinal fluid (CSF), pH 7.33, prepared as described by Cridland and Henry [*Brain Res.* 381:93–99 (1986)]; and injected in a volume of 10 ul followed by 10 ul of artificial CSF to flush the catheter. Drug administrations were completed within 1 min and were followed by analgesic testing beginning at the 5 min time point. Substance P (SP) was obtained from Peninsula Laboratories, Belmont, Calif., and was further purified to homogeneity by HPLC, as described by Kream and coworkers [*Proc. Natl. Acad. Sci. USA* 82:4832–4836 (1985)]. Substance P-Glycine (SP-G) was enzymatically generated from synthetic SP-Glycine-Lysine (Peninsula), and purified to homogeneity by HPLC. Stock concentrations of HPLC-purified peptides were determined by amino acid analysis, as well as comparative chromatogram peak height ratios. Working solutions of morphine sulphate (MS) and the opioid antagonist naloxone were prepared as previously indicated [Chang et al., *Anesthesiology* 70:672–699 (1989)].

Analgesic testing: Animals were given one week in which to recover from surgery, during which time they were habituated daily to the laboratory environment and analgesic testing apparatus. For assessment of thermal nociceptive response, a custom-made tail-flick apparatus (Department of Medical Engineering, Tufts-New England Medical Center) consisted of a variable intensity 300 W quartz projector bulb focused approximately 2 cm from the underside of the tail and a photodetector-automatic timer sensitive to 0.01 sec intervals. Latency to respond following the onset of the radiant heat stimulus applied to the tail was monitored via a visible twitch or flick, which in turn activated the photodetector. Light intensity was adjusted to yield a mean baseline latency of approximately 3.5–4.5 sec, and automatic cutoff was set at 10 sec to avoid damage to the tail. Before each drug trial, a series of 3 pre-drug administration latency measurements were made to establish a stable baseline. Typically, these values varied by less than 10%. Post-drug latency measurements were performed at: 5, 15, 30, 45, 60, 75, and 90 min. The respective differences between the baseline and post-drug latencies constituted the time-dependent analgesic response profile. Difference values where further normalized as % maximum possible effect (MPE) units, according to the following formula: %MPE= 100 × [TF-BL]/[10.0-BL], were TF equaled the post-drug tail-flick latency, BL equaled the baseline latency, and 10.0 represented the cutoff time. Data from the treatment groups were evaluated using ANOVA followed by post hoc testing using the Bonferroni method via the GraphPad InStat program.

Results

Experiment 1

FIG. 1 shows the time-dependent analgesic responses after intrathecal administration of a relatively low concentration of MS (0.1 ug, open triangles) or the same concentration of MS in combination with SP (0.1 ug and 10 pmol, respectively, filled triangles). By comparison, the administration of SP alone (10 pmol) or of artificial CSF (open and filled circles, respectively) produced insignificant changes in tail-flick latencies. Ordinal values within FIG. 1 represent tail-flick latency measurements normalized as % maximum possible effect (MPE), means±S.E.M., as defined in Methods, above; N=10 for each of the four groups. The absence of an error bar indicates that the value of the S.E.M. is smaller than the size of the specified symbol. Whereas MS alone produced a modest analgesic response peaking at approximately 30% MPE, the combination of MS; and SP produced maximal responses at 5, 15 and 30 min. It will be noted that the analgesic response produced by MS in combination with SP was essentially eliminated by pretreatment with intrathecally administered naloxone at 1.0 ug, N=6 (FIG. 1, open squares, dotted trace). Naloxone was given 10 min prior to administration of MS and SP; and the data shows **$P<0.001$, * $P<0.01$, significantly different from SP alone and artificial CSF treatment groups. The MS and MS+SP treatment groups were also significantly different from each other ** $P<0.001$, at 5, 15, 30, and 45 min.

Thus, coadministration of 0.1 ug MS (equivalent to 300 pmol morphine base) and 10 pmol SP into rat CNS by the intrathecal route produced a maximal analgesic response, as reflected in tail-flick latency reaching cutoff at the 5, 15 and 30 min time points, with return to baseline after 60 min. The magnitude of the analgesia was considerably greater in a statistically significant manner than that produced by an equivalent intrathecal administration of MS alone at 0.1 ug through the 45 min time point. Integration of the respective response curves between 5 and 60 minutes demonstrated that the combination of agents provided an approximate 4-fold increase in analgesic potency, as compared to MS alone.

Experiment 2

Figure 2:
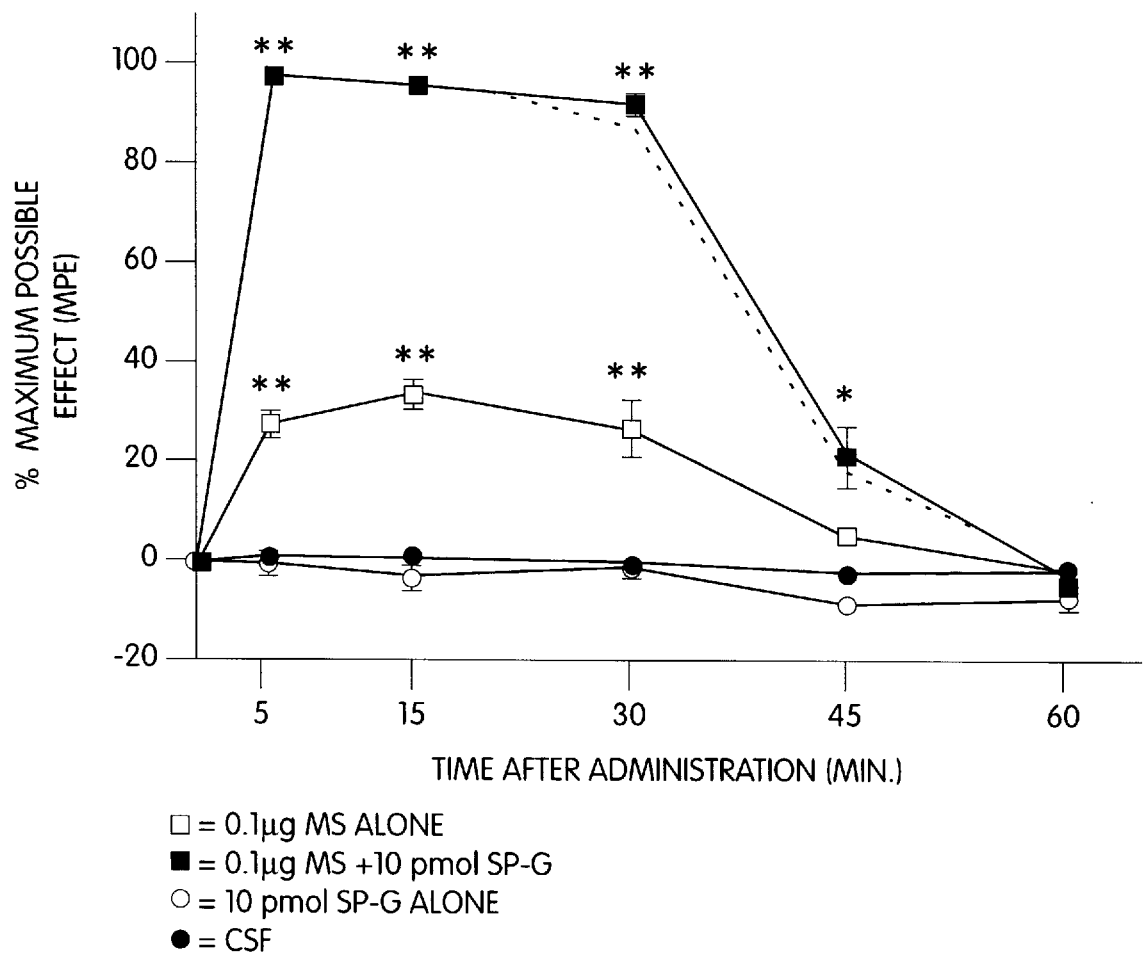
FIG. 2 is a graph illustrating the time-dependant analgesic response of live rats after intrathecal administration of 0.1 ug of morphine sulfate alone or in combination with 10 pmol of the unamidated precursor substance P-Glycine.

A very similar analgesic response is presented by the data of FIG. 2 which reports the time-dependent analgesic responses after intrathecal administration of MS (0.1 ug, open squares) or MS in combination with the unamidated precursor SP-G (0.1 ug and 10 pmol, respectively, filled squares). Administration of SP-G alone (10 pmol) and artificial CSF are represented by open and filled circles, respectively. Ordinal values within FIG. 2 are as defined above, N=6 for each of the four groups. For comparative purposes, an additional group of 6 animals was treated with 0.1 ug MS+10 pmol SP (broken trace), yielding an analgesic response curve that was indistinguishable from that produced by the combination of MS and SP-G. ** $P<0.001$, * $P<0.01$, significantly different from SP-G alone and artificial CSF treatment group were observed. The MS and MS+SP-G treatment groups were also significantly different from each other, ** $P<0.001$, at 5, 15, and 30 min, and * $P<0.01$, at 45 min.

Thus, coadministration of 0.1 ug MS and 10 pmol of the unamidated putative precursor to SP, i.e., the dodecapeptide SP-Glycine (SP-G) yielded an intensity and duration of effect which were indistinguishable from that produced by the combination of MS and SP as shown in FIG. 1. By comparison, control injections of SP or SP-G alone at 10 pmol, or CSF vehicle, produced no measurable analgesic response at these same time points.

Experiment 3

Figure 3:
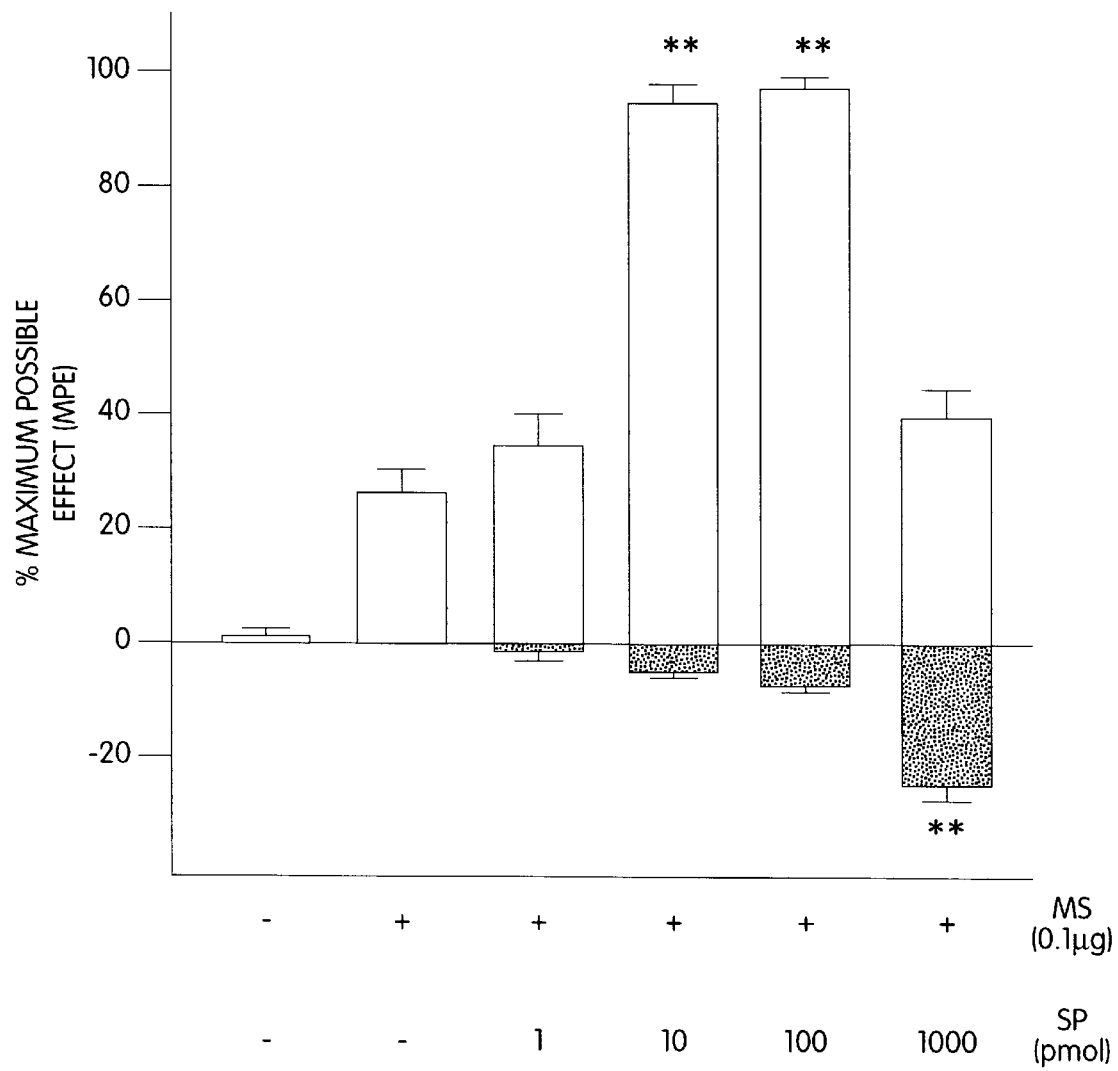
FIG. 3 is a graph illustrating the dose-dependency of the substance P-mediated potentiation of morphine sulfate analgesia in live rats using a set 0.1 ug concentration of morphine sulphate and varying concentrations of substance P ranging between 0.0–1000.0 pmol.

The dose-dependency of the observed phenomenon is revealed by the data of FIG. 3. Normalized changes in tail-flick latencies represented as % MPE were monitored 15 min after administration of increasing doses of SP in combination with a set concentration of 0.1 ug MS (upper set of open bars). The effects of increasing doses of SP alone on tail-flick latencies are represented by the lower set of filled bars. Ordinal values within FIG. 3 are as defined above; N=6 for all of the treatment groups. The maximal analgesic effects of SP either at 10 or 100 pmol in combination with 0.1 ug MS were significantly different,  $P<0.001$, from those observed in all of the other treatment groups. The hyperalgesic effect produced by administration of 1000 pmol of SP alone (represented as a −25% change in MPE) was significantly different,  $P<0.001$, from those observed in the respective treatment groups receiving 1, 10, and 100 pmol SP alone.

It will be noted and appreciated that, at a set concentration of 0.1 ug MS, the peptide-mediated potentiation of opioid analgesia was maximal at 10 to 100 pmol coinjected SP, with measurable but marginal efficacy at 1 and 1000 pmol. Thus, the SP dose-response curve appears to be of a bell-shaped or inverted-U configuration effective over the range of 1–1000 pmol. Moreover, the marginal effect and potentiation of MS by 1000 pmol SP is believed to be due to the statistically significant hyperalgesic effect produced by administration of this relatively high dose.

The stoichiometric relationship between MS and SP is also demonstrated by the data presented in FIG. 3. A very low threshold for MS potentiation and activation by SP is shown, as reflected in a maximal effect of coadministered MS and SP at a stoichiometric ratio of 1:30.

Experiment 4

Figure 4:
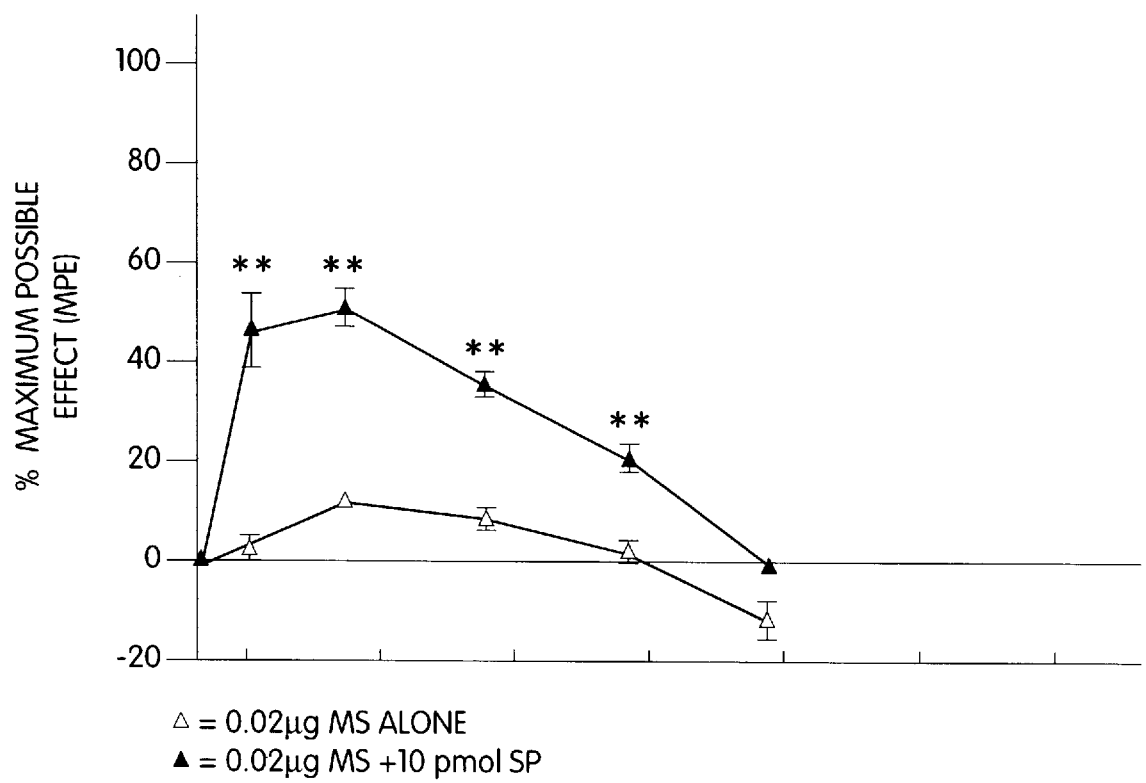
FIG. 4 is a graph illustrating time-dependant analgesic responses of live rats after intrathecal administration of 0.02 ug of morphine sulphate alone or in combination with 10 pmol of substance P.

The analgesic responses elicited by low and high concentrations of MS in combination with a set concentration of 10 pmol SP were then assessed. FIG. 4 shows the time-dependent analgesic responses after intrathecal administration of a very low concentration of MS (0.02 ug, open triangles) or the same 0.02 ug concentration of MS in combination with 10 pmol of SP (filled triangles). Whereas administration of this concentration of MS alone produced a weak response, addition of SP resulted in a strong 6-fold enhancement of opioid analgesia, as quantified by integration of the respective response curves.

Experiment 5

Figure 5:
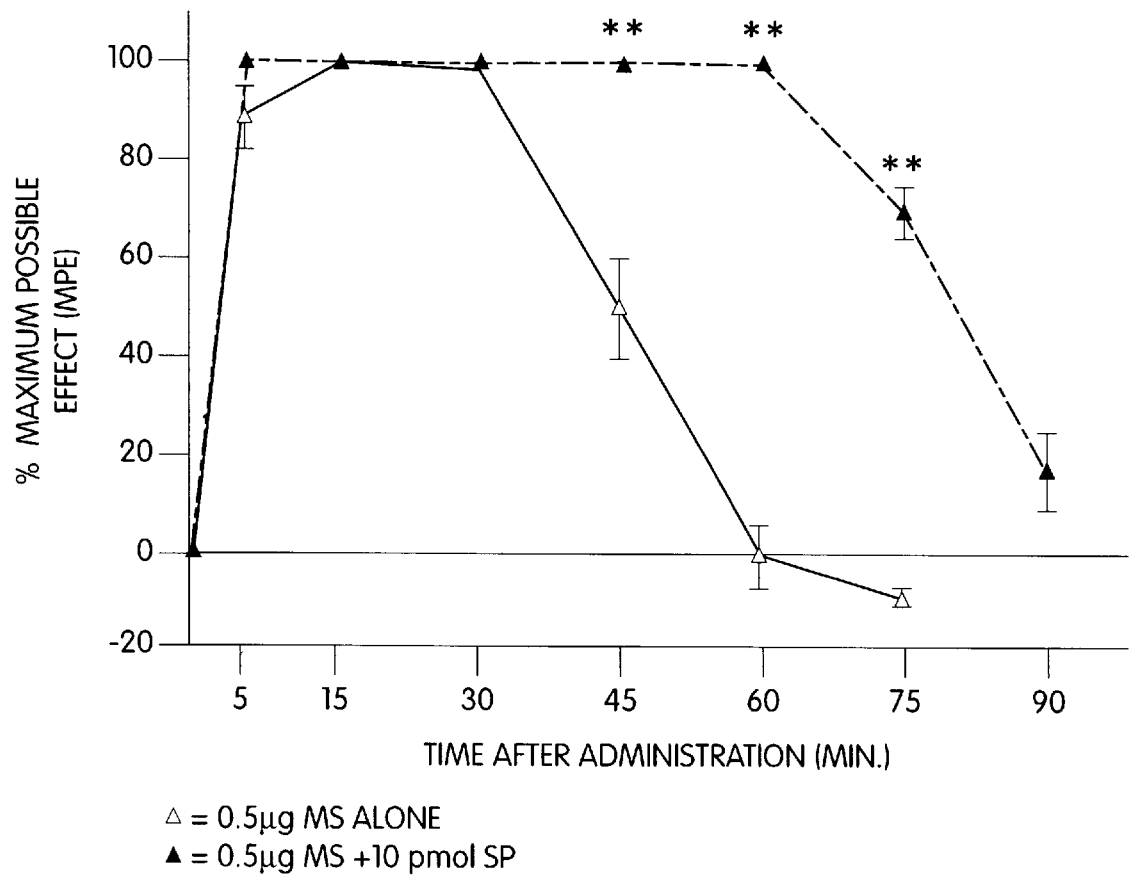
FIG. 5 is a graph illustrating the time-dependant analgesic responses of live rats after intrathecal administration of 0.5 ug of morphine sulfate alone or in combination with 10 pmol of substance P.

The result of FIG. 4 is directly comparable to and contrasted by the data of FIG. 5, which reveals the time-dependent analgesic responses after intrathecal administration of a high concentration of MS (0.5 ug, open triangles) or the same concentration of MS in combination with 10 pmol of SP (filled triangles). Administration of 0.5 ug MS alone elicited a maximal analgesic response between 5 and 30 min which declined to baseline at 60 min (open triangles). T he same 0.5 ug concentration of MS in combination with 10 pmol of SP resulted in a 2-fold enhancement in analgesic potency, as compared to MS alone. For both FIGS. 4 and 5, ordinal values are as defined above; N=6 for all of the treatment groups; ** $P<0.001$, significantly different from the MS treatment groups.

Thus the results presented collectively by FIGS. 4 and 5 demonstrate that at a relatively ineffective dose of 0.02 ug MS, a strong SP-mediated enhancement of opioid analgesia was observed. The potentiation of the analgesic response was approximately 6-fold, as determined from the integration values for the respective response curves. In contrast, a dose of 0.5 ug MS alone elicited a maximal analgesic response between 5 and 30 min which declined to baseline at 60 min; and this same concentration of MS in combination with SP resulted in an approximate 2-fold increase in analgesic potency, as described by extended duration of the maximal response and a prolongation of the time of effect out to 90 min. Overall, therefore, the peptide-mediated potentiation of opioid analgesia was more effectively realized at the lower doses of administered MS (0.02 and 0.1 ug vs. 0.5 ug), thereby indicating a synergistic relationship between the two in producing a biological response at the spinal level.

Experiment 6

Figure 6:
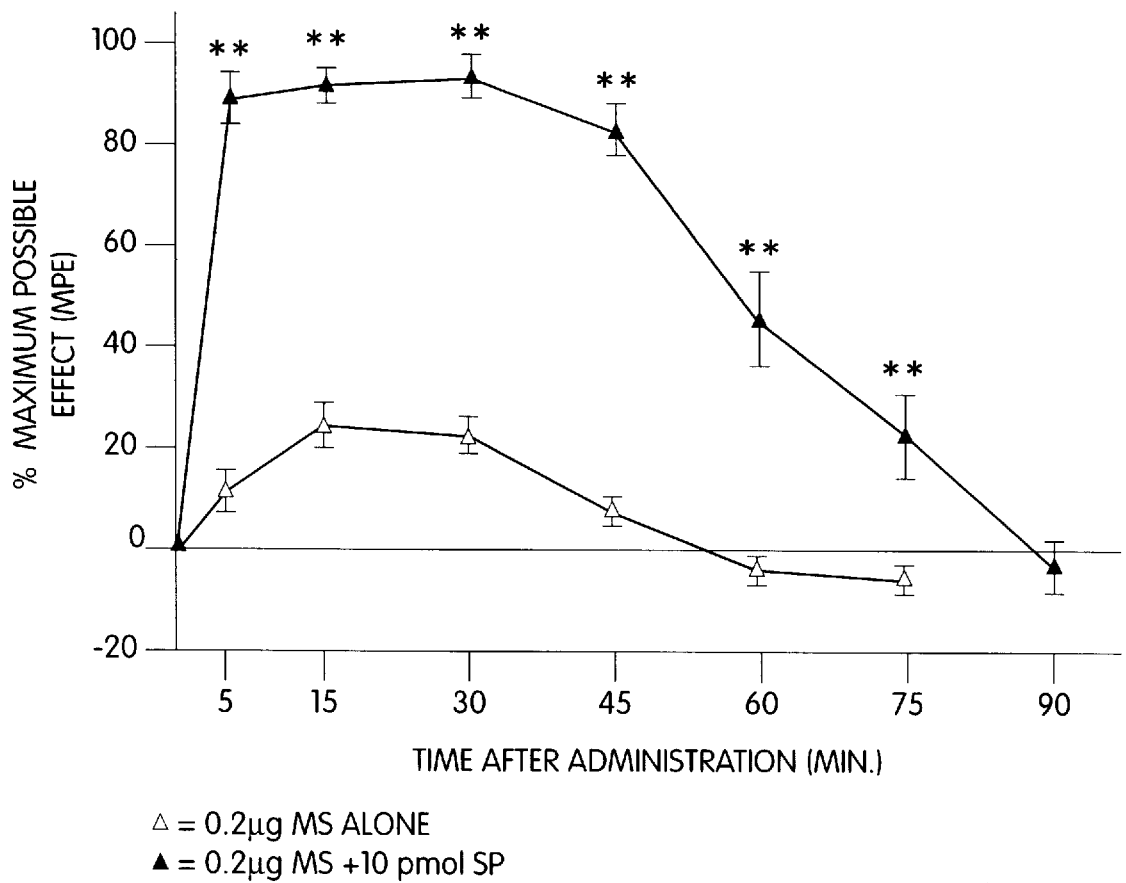
FIG. 6 is a graph illustrating the time-dependent analgesic responses of live rats with spinal cord transection after intrathecal administration of 0.2 ug of morphine sulphate alone or in combination with 10 pmol of substance P.

To assess the role of opioid-responsive descending spinal systems in the development of the potentiated analgesic response, a comparable pharmacological experiment was performed on animals with acute spinal cord transections. The results are presented by FIG. 6 which shows the time-dependent analgesic response after intrathecal administration of MS (0.2 ug, open triangles) or MS in combination with SP (0.2 ug and 10 pmol, respectively, filled triangles) to animals with acutely transected spinal cord. In the spinally transected rate, the SP-mediated potentiation of opioid analgesia was significantly amplified, as compared to the normal case as shown in FIG. 1. The combination of MS and SP produced a maximal response with extended duration from 5 to 45 min and prolonged time of effect. Integration of the respective response curves indicated that MS in combination with SP produced a 6-fold enhancement in analgesic potency, as compared to the use of MS alone. Ordinal values of FIG. 6 are as defined above; N=6 for all of the treatment groups; ** $P<0.001$, significantly different from the MS treatment group.

It is also noteworthy that in this instance it was necessary to administer a twofold higher concentration of MS to achieve a modest analgesic response equivalent to that observed in the intact animal (0.2 ug vs 0.1 ug). Moreover, in the spinally transected rat, the SP-mediated potentiation of opioid analgesia was not only preserved, but significantly amplified, demonstrating an unusually strong effect localized to the spinal cord.

Experiment 7

Figure 7:
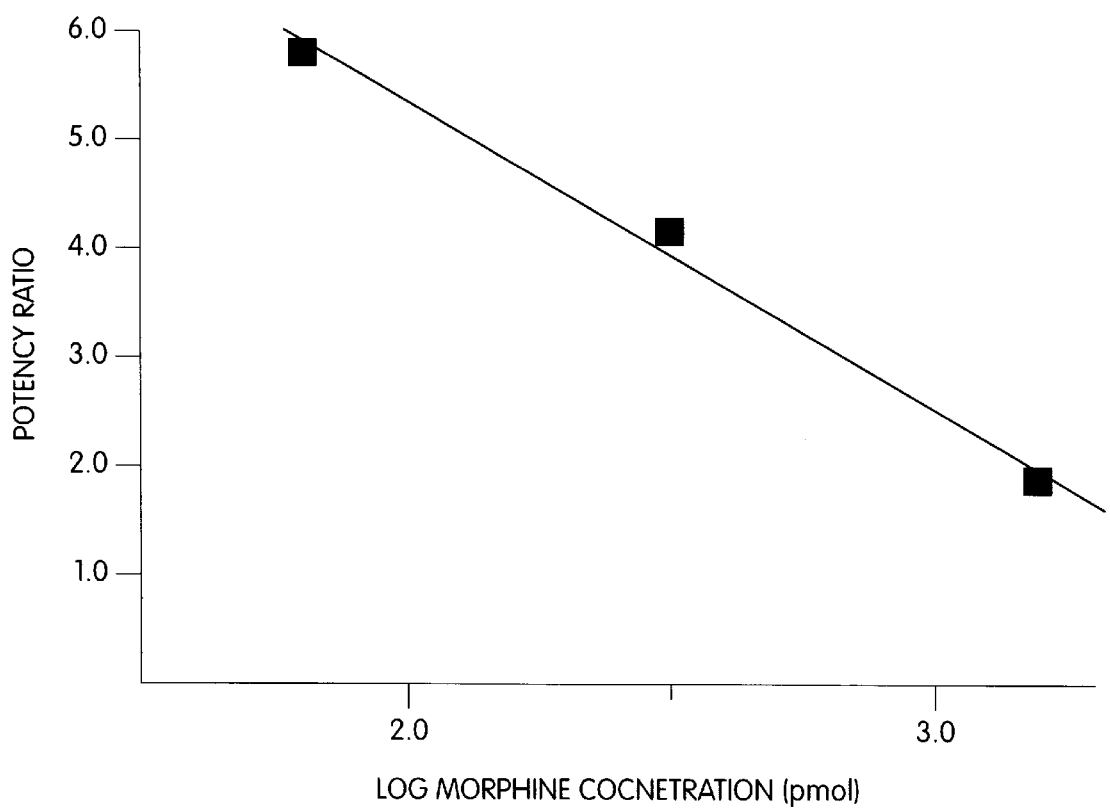
FIG. 7 is a graph illustrating the potency ratio of the substance P-mediated enhancement of morphine sulfate elicited analgesia as a function of concentration.

The SP-mediated fold enhancement of MS-induced analgesia is observed and plotted as a function of MS concentration within FIG. 7. At each tested concentration (60, 300, and 1500 pmol MS), the potency ratio was defined as the ratio of the analgesic response produced by MS in combination with 10 pmol SP to the respective analgesic response produced by MS alone. Analgesic responses were determined by integrating the mean response curves between 5 and 45 min, as obtained from testing of separate treatment groups of rats, N=6. Potency ratios plotted against the log of the MS concentration yielded a linear function varying inversely with administered dose of MS.

As the plot of FIG. 7 demonstrates, there exists a very low threshold for potentiation and enhancement of MS by SP. The respective stoichiometries as also shown in FIG. 3 (of 1:30–1:60 ) reveal here a potency ratio of up to 6 fold, the rate of potency increase and enhancement varying with the MS dose.

As it appears in FIG. 7, the combined analgesic response, normalized as a potency ratio or peptide-mediated fold enhancement of MS-induced analgesia, was plotted as a function of MS concentration. A maximal 6-fold peptide-mediated potentiation of the analgesic response was observed at a threshold dose of 60 pmol MS, declining to approximately a 2-fold potentiated response at 1500 pmol MS. The apparent inverse relationship of potency ration to administered dose of MS appears to be characteristic synergistic relationship between the two compositions in producing analgesia at the spinal level, repeating the overall information derived from FIGS. 4 and 5.

Conclusions

1. The empirical data demonstrate an in-vivo pharmacological relationship in which picomole amounts of SP markedly potentiate the analgesic potencies of modest and even relatively ineffective doses of MS in the range of 0.1 ug. The ability of the opioid antagonist naloxone to effectively block the potentiated analgesic response strongly indicates a convergence of pharmacological effects through opioid-responsive neurons. In addition, the SP-mediated potentiation of opioid analgesia in-vivo is unaffected by actual transection of the spinal cord, thereby indicating the lack of descending supraspinal modulation of the observed phenomenon.

2. The combined data presented here provide in-vivo evidence that spinal tachykinin and opioid systems have a direct: functional interaction in the modulation of local nociceptive responses. The data also indicate that the putative immediate precursor form of SP, (SP-G) is fully active and may substitute for the mature compound in the potentiated pharmacological effect, suggesting that other precursors and modified analogs of SP will be of great utility.

3. The potentiation and enhancement effect of SP upon MS is greatest at a stoichiometric ratios of 1:30.

4. The potency ratio for enhancement of MS is shown to be a 6-fold increase at very low concentrations of MS and a 2-fold increase at higher concentrations of MS.

The present invention is not to be limited in scope nor restricted in form except by the claims appended hereto.

What I claim is:

1. A method for enhancing an opioid analgesia within a living human subject, wherein said enhancing has a duration of at least 15 minutes, said method consisting essentially of the steps of:

administering at least one pharmacologically active opioid selected from the group consisting of morphine and morphine-related opioid agonists to the living subject at a concentration which by itself is a pharmacologically marginal to ineffective picomolar concentration ranging from about 10 pmol/kg to about 10,000 pmol/kg of body weight, said administration being selected from the group consisting of subcutaneous and parenteral administrations;

concurrently administering at least one enhancing agent selected from the group consisting of substance P and its pharmacologically active precursors and analogues to the living subject at a concentration which by itself is a pharmacologically ineffective picomolar concentration ranging from about 0.1 pmol/kg to about 100 pmol/kg of body weight and in a ratio ranging from about 1:10 to 1:100 with respect to said administered opioid concentration, said concurrent administration being selected from the group consisting of subcutaneous and parenteral administrations; and allowing said concurrently administered enhancing agent to interact with and enhance said administered opioid in-vivo such that an effective opioid analgesia results within the living subject.

2. The method as recited in claim 1 wherein said concentration of said administered opioid is from about 10 pmol/kg to about 100 pmol/kg of body weight.

3. The method as recited in claim 1 wherein said administration is parenteral.

4. The method as recited in claim 1 wherein said administration is subcutaneous.

5. A method for enhancing an opioid analgesia within a living human subject, wherein said enhancing has a duration of least 15 minutes, said method consisting essentially of the steps of:

administering at least one pharmacologically active opioid selected from the group consisting of morphine and morphine-related opioid agonists to the living subject at a concentration which by itself is a pharmacologically marginal to ineffective picomolar concentration ranging from about 10 pmol to about 1000 pmol total opioid, said administration being selected from the group consisting of spinal and epidural administrations;

concurrently administering at least one enhancing agent selected from the group consisting of substance P and its pharmacologically active precursors and analogues to the living subject at a concentration which by itself is a pharmacologically ineffective picomolar concentration ranging from about 1.0 pmol to about 1000 pmol total of enhancing agent and in a ratio ranging from about 1:10 to 1:100 with respect to said administered total opioid concentration, said concurrent administration being selected from the group consisting of spinal and epidural administrations; and allowing said concurrently administered enhancing agent to interact with and enhance said administered opioid in-vivo such that an effective opioid analgesia results within the living subject.

6. The method as recited in claim 5 wherein said administration is at the spinal level into the subarachnoid space.

7. The method as recited in claim 5 wherein said administration is epidural.

8. The method as recited in claim 1 or 5 wherein said morphine-related opioid agonists are selected from the group consisting of dihydromorphine, hydrocodone, oxymorphone, fentanyl citrate, sulfentanil, meperidine, butorphanol, and bremazocine.

9. The method as recited in claim 1 or 5 wherein said enhancing agent is one selected from the group consisting of natural precursors of substance P and synthetic precursors of substance P.

10. The method as recited in claim 1 or 5 wherein said enhancing agent is an analogue selected from the group consisting of substance P analogues comprising at least one D-amino acid and substance P analogues comprising a disulfide bridge.

11. The method as recited in claim 1 or 5 wherein said opioid and said enhancing agent are coadministered to the living subject.

12. A method for enhancing an opioid analgesia within a living human subject, wherein said enhancing has a duration of at least 15 minutes, said method consisting essentially of the steps of:

administering at least one pharmacologically active opioid selected from the group consisting of morphine and morphine-related opioid agonists to the living subject at a concentration which by itself is a pharmacologically marginal to ineffective picomolar concentration ranging from about 10 pmol to about 1000 pmol total opioid, said administration being selected from the group consisting of spinal and epidural administrations;

concurrently administering at least one enhancing agent selected from the group consisting of substance P and its pharmacologically active precursors and analogues to the living subject at a concentration which by itself is a pharmacologically ineffective picomolar concentration ranging from about 0.1 pmol/kg to about 100 pmol/kg of body weight and in a ratio ranging from about 1:10 to 1:100 with respect to said administered opioid concentration, said concurrent administration being selected from the group consisting of subcutaneous and parenteral administrations; and allowing said concurrently administered enhancing agent to interact with and enhance said administered opioid in-vivo such that an effective opioid analgesia results within the living subject.

* * * * *